United States Patent [19]

Brown

[11] Patent Number: 4,713,380

[45] Date of Patent: Dec. 15, 1987

[54] PRODUCTION OF OPTICALLY PURE ORGANOBORANES

[75] Inventor: Herbert C. Brown, West Lafayette, Ind.

[73] Assignee: Aldrich-Boranes, Inc., Milwaukee, Wis.

[21] Appl. No.: 692,046

[22] Filed: Jan. 16, 1985

[51] Int. Cl.$^4$ ................................................ C07F 5/02
[52] U.S. Cl. .......................................... 568/1; 568/6; 568/7
[58] Field of Search ..................................... 568/1, 6, 7

[56] References Cited

U.S. PATENT DOCUMENTS

| | | | |
|---|---|---|---|
| 3,254,129 | 5/1966 | Brown | 568/7 X |
| 3,337,643 | 8/1967 | Lerner et al. | 568/1 X |
| 3,358,034 | 12/1967 | Brown | 568/1 X |
| 4,082,810 | 4/1978 | Brown | 568/6 |

OTHER PUBLICATIONS

Brown et al, JACS, 106, 1797–1800, (1984).
Brown et al, JACS, 105, 2092–2093, (1983).
Brown et al, J. Org. Chem., 47, 5065–69, (1982).
Brown et al, J. Org. Chem., 47, 5069–74, (1982).
Brown et al, J. Org. Chem., 47, 5074–83, (1982).
Chemical Abstracts, 65, 7206e, (1966).
Brown et al, J. Org. Chem., 47, 4583–84, (1982).

*Primary Examiner*—Helen M. S. Sneed
*Attorney, Agent, or Firm*—Niblack & Niblack

[57] ABSTRACT

A process for upgrading to essentially 100% enantiomeric excess the optical purity of an organoborane intermediate represented by the formulae:

$$IcpBHR^*$$

or $$Icp_2BR^*$$

wherein Icp is isopinocampheyl and R* is a unsubstituted or substituted, acyclic or cyclic alkyl having from 4 to 30 carbon atoms, comprising the steps of hydroborating cis-alkene, a trans-alkene or a tertiary-alkene with monoisopinocampheylborane or diisopinocampheylborane, obtaining a solid organoborane and recrystallizing the solid organoborane to obtain an enantiomeric excess of essentially 100% ee of said organoborane.

32 Claims, 13 Drawing Figures

PRODUCTION OF OPTICALLY PURE ORGANOBORANES

BACKGROUND OF THE INVENTION

(I) Field of Invention

The present invention relates to an improved method for converting organoboranes containing a partially optically active organyl group attached to boron, and more specifically relates to methods and intermediates for the asymmetric hydroboration of cis-alkenes, trans-alkenes and tertiary-alkenes to organoboranes containing an essentially optically pure organyl group.

Asymmetric hydroboration of alkenes, with either diisopinocampheylborane or monoisopinocampheylborane typically provides the corresponding chiral organoborane containing the new alkyl group, R*, in from 50 to 90% enantiomeric excess (ee), and occasionally in purities of from 90 to 100% ee. Because of the importance of hydroboration to, for example, the pharmaceutical industry, there has been a long standing need for a simple, reliable process which provides the alkyl group, R*, in 100% ee in all cases. The present invention fulfills that need in cases involving cis-alkenes, trans-alkenes, tertiary-alkenes and the hydroborating agents diisopinocampheylborane and monoisopinocampheylborane.

(II) Description of the Prior Art

Figure 1:
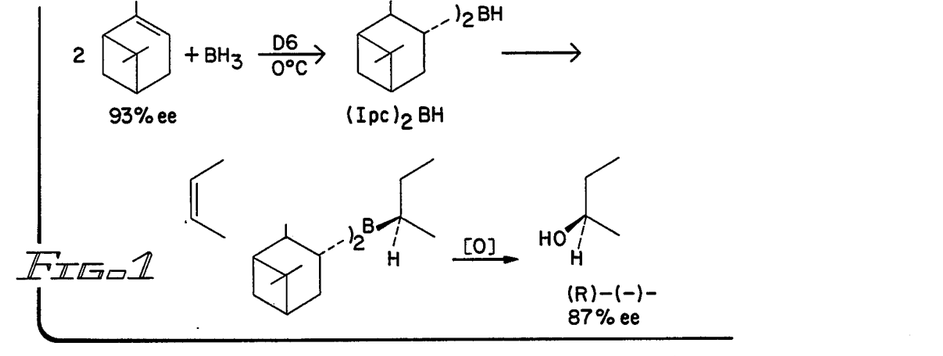
FIG. 1 is a reaction scheme of the original asymmetric hydroboration.
Figure 2:
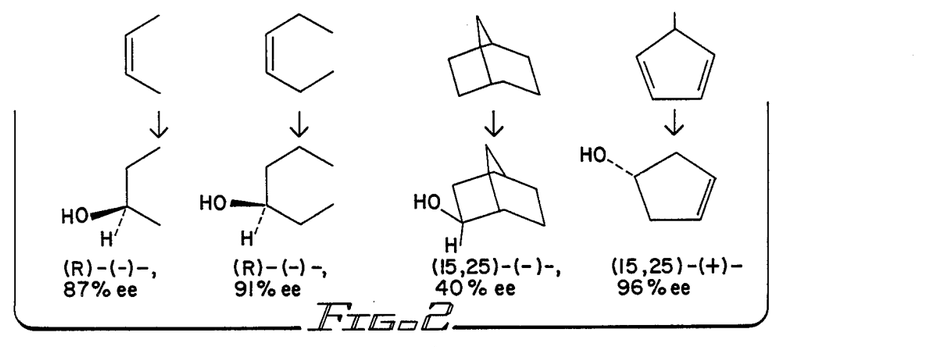
FIG. 2 is a reaction scheme of representative asymmetric hydroboration of cis-alkenes.

The first successful asymmetric synthesis occured in 1961 with the hydroboration of cis-2-butene in diglyme (DG) by the chiral dialkylborane, diisopinocampheylborane to yield 2-butanol of 87% ee. Brown, H. C. et al., J. Am. Chem. Soc. 86, 397 (1964). Diisopinocampheylborane (Ipc$_2$BH) was prepared by the hydroboration of (+)− and (−)-α-pinene. See Brown, H. C. and Zweifel, G., J. Am. Chem. Soc., 83. 486 (1961). (FIG. 1). That landmark achievement not only provided a remarkably high asymmetric synthesis, the first of its kind, but further provided a reagent which appeared generally applicable to the asymmetric hydroboration of cis-alkenes. Brown, H. C. et al, JACS 86, 397 (1964) and Partridge, J. J., et al, JACS 95, 532 (1973). (FIG. 2)

Figure 3:
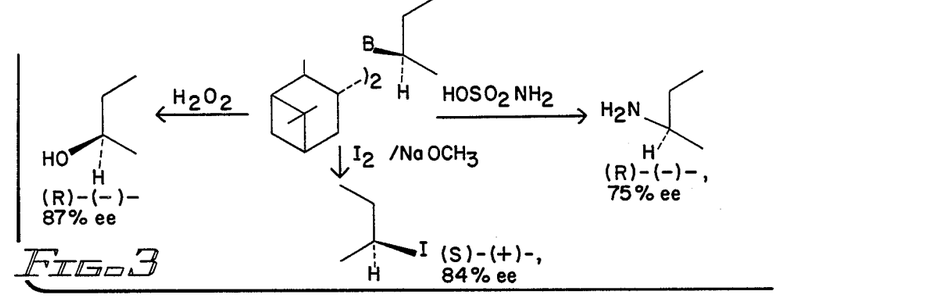
FIG. 3 is a reaction scheme of representative conversions of the chiral intermediate, 2-butyldiisopinocampheylborane to optically active 2-aminobutane with complete retention of configuration and 2-iodobutane with complete inversion of configuration and which is applicable to many syntheses.

The chiral intermediate, 2-butyldiisopinocampheylborane, was subsequently converted into optically active 2-aminobutane with complete retention of configuration and into 2-iodobutane with complete inversion of configuration. Verbit, L. et al, JOC 32, 3199 (1967) and Brown, H. C. et al, JASC 98, 1290 (1976). (FIG. 3).

Figure 4:
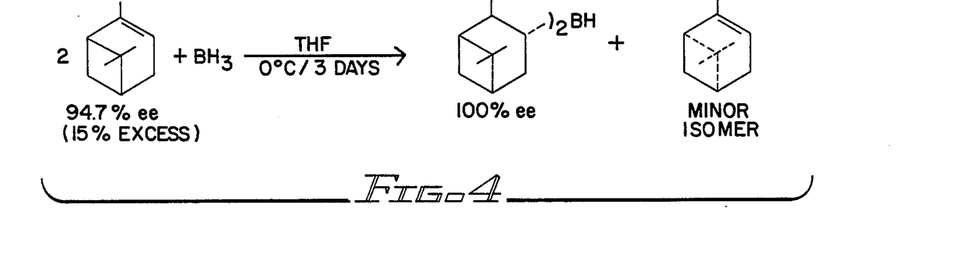
FIG. 4 is a reaction scheme of the preparation of optically pure diisopinocampheylborane (100% ee)
Figure 5:
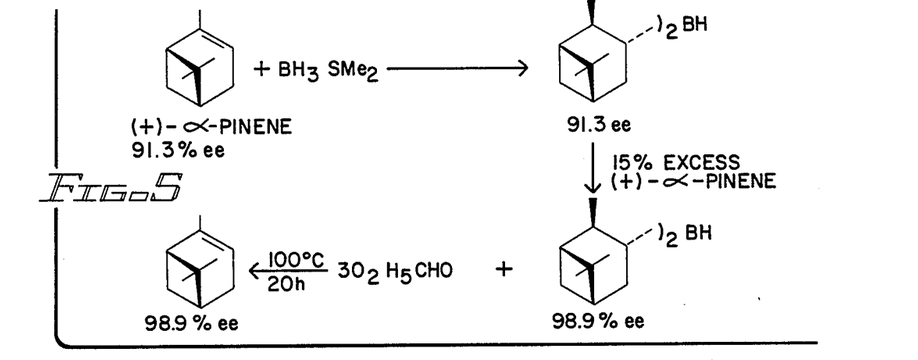
FIG. 5 is a reaction scheme of a convenient procedure for upgrading (+)- and (−)-α-pinene to material of high optical purity.

In the original study of hydroborations with optically active diisopinocampheylborane, the reagent employed was prepared from commercial α-pinene of relatively low enantiomeric purity (~93%). Subsequent advances resulted in the preparation of reagent of high enantiomeric purity from such α-pinene. The reagent is equilibrated at 0° C. with 15% excess α-pinene. The major isomer becomes incorporated into the crystalline reagent, leaving the minor isomer in solution. Brown, H. C. et al, Israel J. Chem. 15, 12 (1977). (FIG. 4). Treatment of the diisopinocampheylborane with benzaldehyde liberated α-pinene of approximately 100% ee. Thus, two reactions were developed which provided a convenient procedure for upgrading the commercial α-pinene to an enantiomeric purity of essentially 100% ee. Brown, H. C. et al, JOC 47, 4583 (1982). (FIG. 5).

Figure 6:
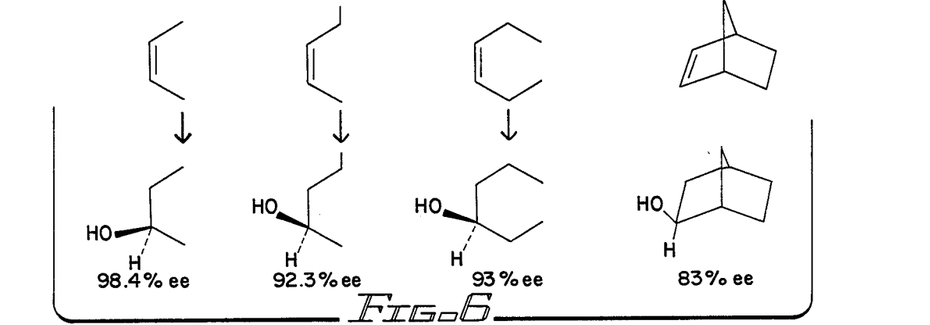
FIG. 6 depicts reaction schemes of representative applications of 100% pure diisopinocampheylborane to the hydroboration-oxidation of cis-alkenes.
Figure 7:
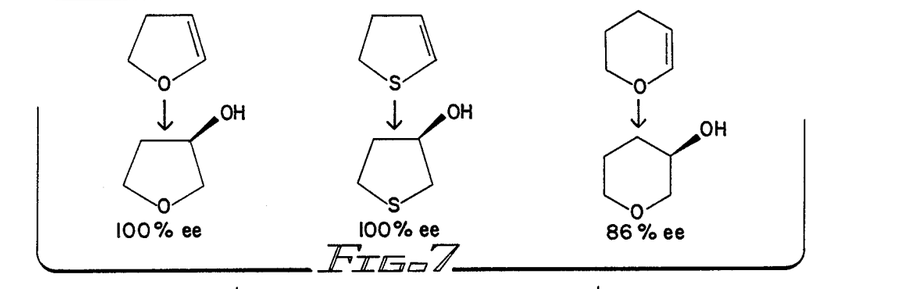
FIG. 7 depicts reaction schemes of representative applications of 100% pure diisopinocampheylborane to the hydroboration-oxidation of heterocyclic olefins.
Figure 8:
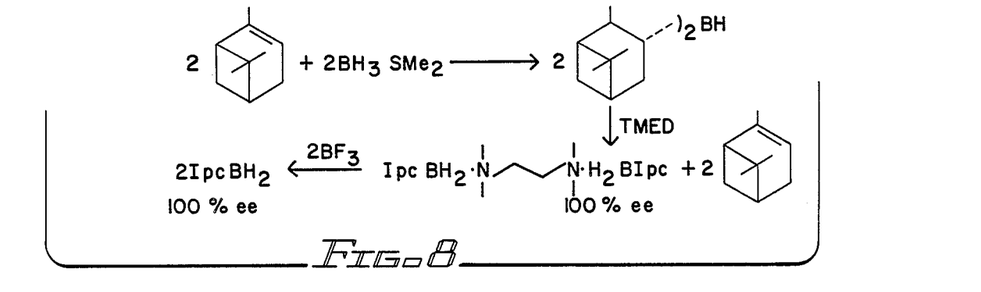
FIG. 8 is a reaction scheme of the preparation of monoisopinocampheylborane of high optical purity.
Figure 9:
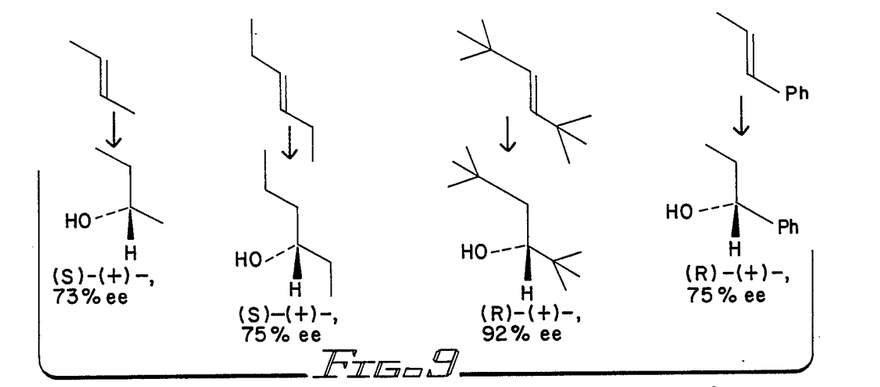
FIG. 9 depicts reaction schemes of representative applications of monoisopinocampheylborane to the hydroboration-oxidation of trans-alkenes.

Improved asymmetric results were achieved in the hydroboration of cis-alkenes with this improved reagent and a somewhat lower hydroboration temperature (−25° C.). Brown, H. C. et al, JOC 47, 5065 (1982). (FIG. 6).

It has been found that while diisopinocampheylborane [(Ipc$_2$BH] handles cis-alkenes very effectively, it is not an effective asymmetric hydroborating agent for trans-alkenes and trisubstituted alkenes and that monoisopinocampheylborane (IpcBH$_2$) is a more effective hydroborating agent for the latter types of alkenes.

It is difficult to halt the hydroboration of α-pinene at the monoalkylborane stage. Consequently, it was found that the monoisopinocampheylborane must be prepared by an indirect route, such as by treating diisopinocampheylborane with one-half molar equivalent of N,N,N,N-tetramethylethylenediamine (TMED) to obtain 2(IpcBH$_2$).TMED. The diastereomeric adduct crystallizes out in enantiomerically pure form, and the pure monoisopinocampheylborane is readily liberated by treating the adduct with boron trifluoride etherate according to the method of Brown, H. C. et al, JOC 43, 4395 (1978).

Figure 10:
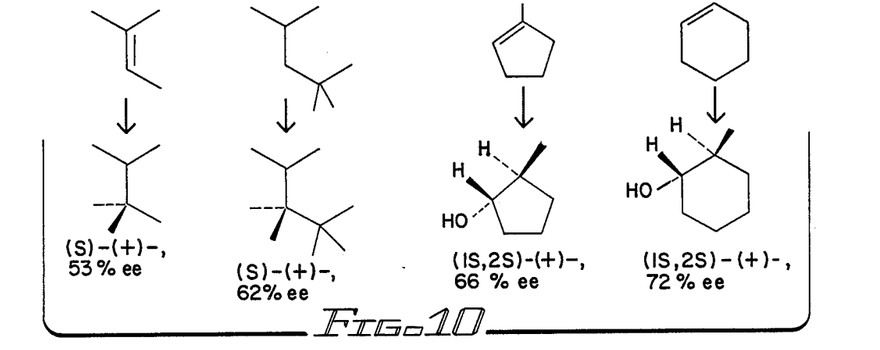
FIG. 10 sets forth representative reaction schemes for the hydroboration-oxidation of trisubstituted alkenes with monoisopinocampheylborane.

Monoisopinocampheylborane has been found to be very effective for the asymmetric hydroboration of trans-alkenes (See Brown, H. C. et al, JOC 46, 5047 (1981) (FIG. 10). Similarly, the hydroboration of trisubstituted alkenes with monoisopinocampheylborane, followed by oxidation of the intermediate organoboranes, provides the corresponding alcohols in 53–72% ee, Brown, H. C. et al, JACS 99, 5514 (1977); Brown, H. C. et al., JOC 47, 5074 (1982) (FIG. 10).

Figure 11:
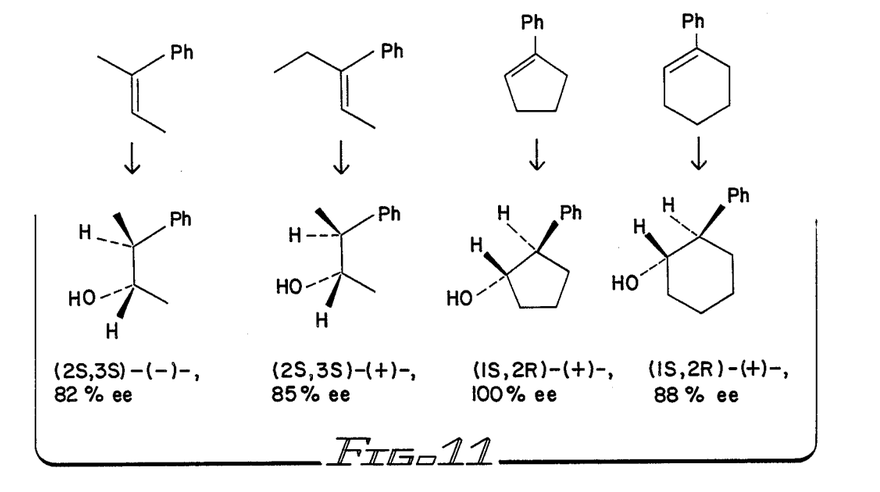
FIG. 11 sets forth representative reaction schemes for the hydroboration-oxidation of phenyl-substituted alkenes.

For reasons that are not understood, the asymmetric hydroboration of the phenyl derivatives provides considerably improved hydroboration products of, for example 82% ee, 85% ee, 100% ee and 88% ee (FIG. 11) as compared to the 53% ee, 62% ee, 66% ee and 72% ee respectively for the corresponding parent compounds (FIG. 10), see Mandal, A. K. et al, JOC 45, 3543 (1980).

Monoisopinocampheylborane and diisopinocampheylborane are complementary to each other, and are capable of handling three of the four major classes of alkenes. Diisopinocampheylborane, a reagent with larger steric requirements, is more suited for use in the case of unhindered cis-olefins. On the other hand, hydroboration of olefins with larger steric requirements proceeds more favorably with a reagent of lower steric requirements, monoisopinocampheylborane. There still remains a need for a suitable reagent which will permit synthesis of products of high enantiomeric excess from alkenes of relatively low steric requirements, such as the 2-methyl-1-alkenes.

Figure 12:
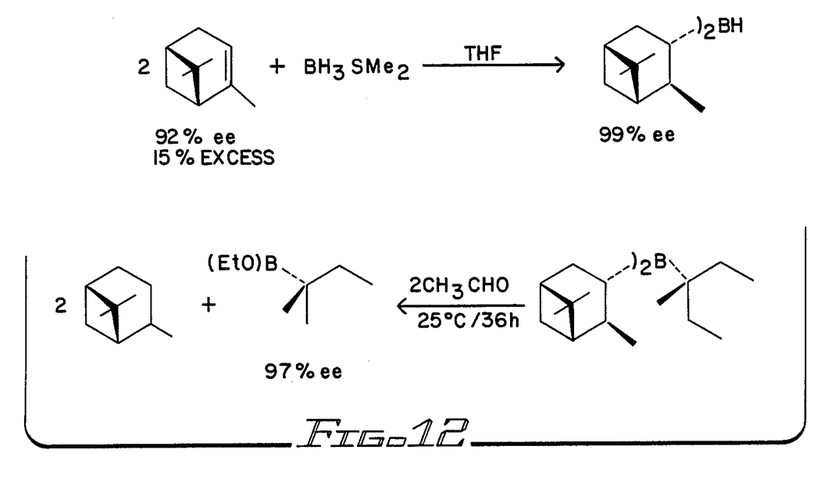
FIG. 12 is a reaction scheme of the direct chiral synthesis of boronic esters using diisopinocampheylborane.

Initially, the application of chiral organoboranes was limited primarily to alcohols because of the presence of isopinocampheyl groups on boron in the product. Recently, it was discovered that these groups can be selectively eliminated by treatment of the mixed chiral organoboranes with acetaldehyde, regenerating the α-pinene, and providing the optically active boronate as the product. In this way, for example, 2-butyldiisopinocampheylborane is readily converted into diethyl 2-butylboranate in 97% ee. Brown, H. C. et al, JACS, 104, 4303 (1982). (FIG. 12)

Figure 13:
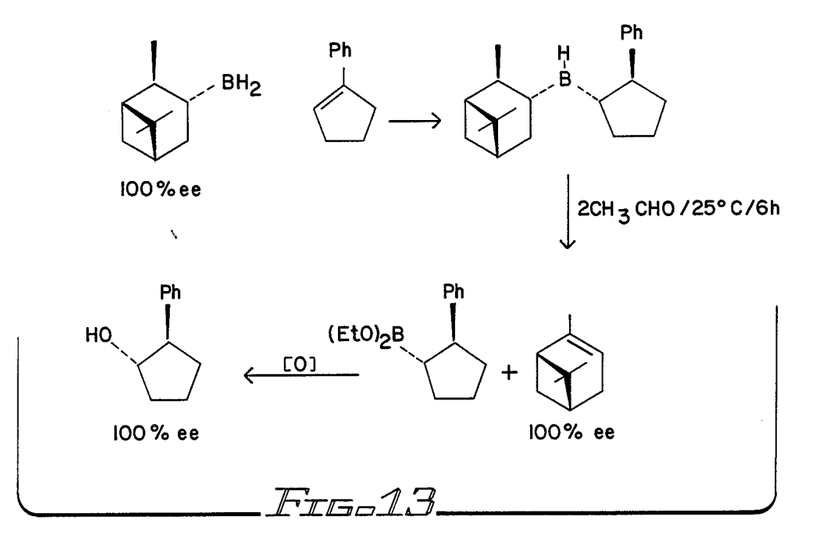
FIG. 13 is a reaction scheme of the direct chiral synthesis of boronic esters using monoisopinocampheylborane.

Similarly, diethyl trans-2-phenylcyclopentylboronate can be obtained in 100% ee by the method of Brown, H. C. et al, JACS 104, 4303 (1982). (FIG. 13).

Hyroboration of prochiral alkenes with diisopinocampheylborane and monoisopinocampheylborane typically results in products in which approximately 60 to 90% optical activity is generally induced in the R*BIpc$_2$ and R*BHIpc. This means that the major isomer is present in large amounts, 80–95%, and the minor isomer in much smaller amounts, 20–50%. The problem is how to separate the major isomer from the small amount of minor isomer present.

The usual organic synthesis of enantiomers produces a 50:50 mixture of the two optical isomers. Normally, these are separated by combining them with a naturally ocurring optically active acid or base (chiral auxiliary) to form a pair of diastereoisomers. Laborious fractional crystallization then separates the two diastereoisomers. The chiral auxiliary is then removed to regenerate the desired optically active compound.

However, it is not always possible to resolve optical mixtures once the final products have been obtained without destroying the molecule, and there has been a longstanding need for a reliable method of resolving the mixture at a stage to obtain an optically pure intermediate which can then be converted to any number of final products while retaining its optical configuration.

It has now been discovered that optionally pure organoborane intermediates can be reliably and readily obtained from trans-alkenes, tertiary-alkenes and monoisopinocampheylborane or cis-alkenes and diisopinocampheylborane by recrystallization of the resulting boron intermediate if solid, or first converting the liquid to a solid according to the process of the present invention. The process of the present invention not only eliminates the necessity of employing a chiral auxiliary to separate the diasteroisomers, but provides the desired organyl groups, R*, in essentially 100%ee. Consequently, the present method provides an advance in the art. By the process of this invention, it is now possible to prepare virtually any optically active compound with a chiral center, either d- or l-, in essentially 100% ee. from a cis-alkene, trans-alkene or dialkene.

SUMMARY OF THE DISCLOSURE

The present invention provides methods for prepareing optically pure organoboranes from cis-alkenes, trans- or tertiary-alkenes and diisopinocampheylborane or monoisopinocampheylborane containing the chiral group R* attached to boron in an optical purity of essentially 100% ee. These optically pure organoboranes are then readily converted into essentially any class of organic compounds, making possible the synthesis of a large number of monochiral organic compounds in an optical purity of essentially 100% ee.

BRIEF DESCRIPTION OF THE DRAWINGS

The invention will be more readily understood by the following description, taken in conjunction with the drawings in which.

DETAILED DESCRIPTION OF PREFERRED EMBODIMENTS

The present invention provides a simple, direct and economical method of producing an optically pure boron intermediate which can be converted to virtually any optically active compound having a chiral center, either d- or l-, in essentially 100% enantiomeric excess. The process of the present invention eliminates the necessity of undertaking laborious fractional crystallization to obtain the desired diasterioisomer.

In one aspect, the process of this invention comprises the producing in essentially 100% enantiomeric excess (ee) an optically pure organoborane comprising the steps of reacting a cis-alkene with the optically active hydroborating agent diisopinocampheylborane, or a trans- or tertiary-alkene with monoisopinocampheylborane, obtaining a solid hydroboration product and recrystallizing said solid hydroboration product from a suitable reagent at low temperature.

In cases where the organoborane resulting from the reaction of a prochiral alkene and the optically active hydroborating agent is a solid, simple recrystallization of the reaction product, with, for example, a hydrocarbon such as pentane or ether, results in the desired organoborane intermediate of essentially 100% enantiomeric excess.

In cases where the organoborane is a liquid, a solid derivative is prepared by forming either a crystalline borate, a borane complex or a chelate.

Crystalline borates are conveniently obtained by treating the liquid organoborane, Ipc$_2$BR*, with a strong base preferably an alkali metal base such as such as LiMe, LiH, LiNMe$_2$, KOMe, KCN, illustrated in the following reaction schemes.

wherein M is an alkali metal and X is selected from the group consisting of hydrogen, lower alkyl, lower alkoxy, CN, NR$_1$R$_2$ wherein R$_1$ and R$_2$ are the same or different members of the group consisting of hydrogen and lower alkyl.

Crystalline borane complexes are readily prepared by reacting the liquid organoborane with an amine of low steric requirements such as ammonia, methylamine, dimethylamine, trimethylamine, pyrrolidine, piperidine, and the like, according to the following reactions schemes:

Ipc$_2$BR* + (CH$_3$)$_3$N → Ipc$_2$R*BN(CH$_3$)$_3$

Ipc$_2$BR* + Py → Ipc$_2$R*BPy wherein Py is pyridine, etc.

Solid chelate derivatives are prepared by reacting the liquid organoborane with an aldehyde to form the borinic acid ester, followed by a suitable chelating agent such as ethanolamine, N-methylethanolamine, 2-pyridylmethanol, 2-pyrrolidinemethanol and similar chelating agents as represented by the following formulae:

Ipc$_2$R*B + R'CHO → IpcR*BOR' + α-pinene

The term "suitable aminoethanol chelating agent refers to compounds represented by the formula RNHCH$_2$CH$_2$OH where R consists of hydrogen, C$_1$ to C$_6$ straight or branched chain alkyl and C$_3$ and C$_6$ cycloalkyl and benzyl.

Alternatively, the liquid hydroboration products, Ipc$_2$BR* can be enriched by selective treatment with an appropriate reagent which preferentially destroys one isomer, permitting an enrichment in the less reactive isomer. This procedure takes advantage of the fact that such compounds contain three different optically active groups. They will therefore exist of at least two different diastereomers with different reactivities. The enrichment with aldehydes, preferably benzaldehyde, is valuable for such enrichments which proceed according to the following general reaction scheme.

Ipc$_2$BR* + C$_6$H$_5$CHO → IpcR*BOCH$_2$C$_6$H$_5$ + α-pinene

Enrichment may also be achieved by carrying out the displacement to produce a mixture of borinic and boronic esters which are readily separated by selective extraction with alkali. The borinic acid is isolated, converted to the methyl ester or trimethylene glycol ester, for example, or oxidized to the alcohol.

In cases where the reaction product of an alkene with monoisopinocampheylborane or diisopinocampheylborane is a solid, direct crystallization by treatment with a suitable solvent, preferably a hydrocarbon such as n-pentane, iso-pentane, or hexane, or an ether such as diethyl ether, tetrahydrofuran or dimethyoxyethane, result in the desired crystalline intermeidate having an enantiomeric purity in excess of 98%ee.

In cases where the reaction product of an alkene with either monoisopinocampheylborane or diisopinocampheylborane is a liquid, e.g. an oil, it is first necessary to convert the reaction product to a solid as described above. The solid borate, borane complex or chelate is then recrystallized by treatment with a suitable solvent to obtain the desired borane intermediate of 98% or greater ee.

As used herein, the term "essentially 100% enantiomeric excess" means an enantiomeric excess of at least 98% of one of the members of an enantiomeric pair.

The term "ee" is an abbreviation for "enantiomeric excess".

The term "enantiomeric pair" refers to a pair of substances whose molecules are nonidentical mirror images.

The term "hydrocarbon" as used herein in referring to a suitable solvent refers to C$_3$ to C$_8$ straight or branched chain or cyclic hydrocarbons, i.e. pentane, hexane, cyclooctane, isobutane and the like, and aromatic hydrocarbons such as benzene or toluene.

The term "alkali metal" includes sodium, lithium and potassium.

The term "ether" refers to dialkyloxides including cyclic derivatives such as diethyl ether, tetrahydrofuran and dimethoxyethane.

The term "R*" refers to an optically active [(+) or (−)] substituted or unsubstituted, cyclic or acyclic alkyl groups having from 4 to 30 carbon atoms. Acyclic alkyl group may be straight or branched chain. Aryl groups may be present.

The term "chiral", as used herein, refers to compounds which lack reflection symmetry, i.e., are not identical with their mirror images.

The term "alkene" refers to acyclic and cyclic alkenes having up to 30 carbon atoms.

The term "alkyl" refers to substituted and unsubstituted, cyclic and acyclic alkyl groups having up to 30 carbon atoms. In the case of acyclic alkyl, the alkyl groups may be straight or branched chain.

Generally speaking, recrystallization of the solid borane intermediate, obtained either directly from reacting a trans- or tertiary-alkene with monoisopinocampheylborane or a cis-alkene with diisopinocampheylborane or, when the reaction product is a liquid, converting the liquid borane into a solid borate, borane complex or chelate as described above, is achieved by treatment with a suitable solvent at temperatures of from −78° C. to about 37° C., preferably from 0° C. to −78° C. and most preferably from about −25° C. to −78° C. While concentration of the solute is not critical, it is generally preferred to use at least 1 molar concentration of solute or higher.

Suitable cooling baths for recrystallization include, for example, pentane slush, dry ice and acetone, dry ice and alcohol, and the like.

The process of this invention resolves at a stage where the resulting optically pure intermediate can be employed to prepare a wide variety of final products having the optical configuration of the optically pure intermediate as shown in the following general reaction scheme:

wherein R* is an optically pure acylic or cyclic, substituted or unsubstituted alkyl group.

The following examples further illustrate this invention.

In the following examples, all operations were carried out under a nitrogen atomsphere with oven-dried glassware. Gas chromatography analyses were carried out with a Hewlett-Packard 5750 chromatograph using either (a) a 6 ft×0.25 in. column packed with 10% Carbowax 20M polyethylene glycol (Union Carbide) on Chromosorb W (60–80 mesh) aluminum oxide support or (b) a 6 ft×0.25 in. column packed with 20% SE-30 silicon oil on Chromosorb W (60–80 mesh) aluminum oxide support. For preparative gas chromotagraphy, either a (c) 6 ft by 0.5 in. column packed with 10% Carbowax 20M polyethylene glycol on Chromosorb W (60–80 mesh) aluminum oxide support, or a (d) 6 ft×0.5 in. column packed with 20% SE-20 silicon oil on Chromosorb W (60–80) were used.

$^{11}$B NMR were recorded on a Varian FT-80A instrument. The chemical shifts are in δ relative to the EE-BF$_3$. Optical rotations were measured on a Rudolph polarimeter Autopol III.

The bis adduct of monoisopinocampheylborane with tetramethylethylenediamine (TMED.2BH$_2$Ipc) was prepared from (+)-α-pinene of 91.6% ee according to the reported procedure of Brown, H. C. et al., *J. Org. Chem.* 1978, 43, 5074. Anhydrous ethyl ether was purchased from Mallinckrodt, Inc. The alkenes employed in the following examples were commercial products of the highest purity available. Lithium aluminum hydride in ethyl ether was purchased from Aldrich Chemical Co.

The optically pure organoboranes provided by this invention are represented by the formulae:

IpcBHR* and

Ipc$_2$BR* wherein Ipc is isopinocampheyl and R* is an optically active (+) or (−) alkyl group.

EXAMPLE 1

Generation of Monoisopinocampheylborane from the Bis-adduct of Monoisopinocampheylborane with Tetramethylethylenediamine in Ethyl Ether A 250 ml flask with a magnetic stirring bar and septum was charged with 20.85 g of TMED.2BH Ipc (50 mmol) and ethyl ether ((67.2 ml). While the slurry was stirred at 24° C., 12 ml (98 mmol) of boron trifluoride etherate (EE.BF$_3$) was added dropwise and the reaction mixture was allowed to stir at 25° C. for 2 hours. Meanwhile, a 250 ml flask with a septum inlet, magnetic stirring bar and a filtration chamber was assembled under dry nitrogen and cooled to 25° C. The resulting slurry from the reaction flask was transferred under nitrogen to the filtration chamber. The solid TMED.2BF was washed with ethyl ether (2×36 ml). The combined filtrate was analyzed for monoisopinocampheylborane by hydrolysis with 1:1:1 glycerol, water and tetrahydrofuran as the hydrolyzing mixture and found to be 0.723M, 110 ml (79.5 mmol), 79% yield. $^{11}$B NMR (decoupled): +22.4(singlet); [α]$^{23}$D −39.93 (c 11.6, ethyl ether). The standard solution of monoisopinocampheylborane in ethyl ether can be stored at 0° C. for at least 20 days without any isomerization or loss of hydride activity.

EXAMPLE 2

Preparation of Isopinocampheyl-(1S,2S)-trans-2-Methylcyclopentylborane

A 50 ml centrifuge vial fitted with a rubber septum and a magnetic stirring bar was charged with 34.6 ml of (−) monoisopinocampheylborane (100% ee) in ethyl ether (0.723M, 25 mmol) and cooled to −35° C. 1-Methylcyclopentene (3.2 ml, 30 mmol) was added and the reactants were thoroughly mixed together and the vial left at −35° C., without stirring, for 12 hours. The supernatant solution was decanted using a double-ended needle. The crystalline isopinocampheyl-(1S,2S)-trans-2-methylcyclopentylborane was washed with cold (−35° C.) ethyl ether (2×5 ml) and dried at 25° C. under reduced pressure (12 mm Hg); 3.79 g (16.3 mmol, 65% yield). The dialkylborane was methanolyzed, oxidized and worked up following the literature procedure of Brown, H. C. et al., *J. Org. Chem.*, 1978, 43, 5074. The (1S,2S)-trans-2-methylcyclopentanol obtained was purified using column d to furnish a GC-pure material: [α]$^{23}$D +46.8° (neat), 100% ee.

EXAMPLE 3

Preparation of Isopinocampheyl-(2S,3R)-3-phenyl-2-pentylborane

Following the procedure of Example 1, 4 ml (25 mmol) of [Z]-3-phenyl-2-pentene was added to 27.2 ml (2 mmol) of 0.92M monoisopinocampheylborane in ethyl ether at −35° C. The final molarity of the reaction mixture was 0.8M. The reactants were mixed well and allowed to stand at −35° C., without stirring, for 12 hours. The impure dialkylborane crystallized from the solution. The supernatant solution containing the optically pure dialkylborane was decanted. The solid was washed with cold ethyl ether (2×3 ml) and dried to yield 1.68 g of product (5.7 mmol, 22.8% yield). The supernatant solution was methanolyzed, oxidized and worked up according to the procedure of Brown, H. C.

et al., *J. Org. Chem.*, 43, 5074 (1978). The (2S,3S)-3-phenyl-2-pentanol obtained was purified using column d to provide a GC-pure sample: $[\alpha]^{23}D$ +24.9° (c 4, C$_2$H$_5$OH), 100% ee.

EXAMPLE 4

Preparation of Isopinocampheyl-(1S,2S)-trans-2-methylcyclohexylborane

Following the procedure of Example 1, 3.5 ml (30 mmol) of 1-methylcyclohexene was added to 34.6 ml (25 mmol) of 0.723M monoisopinocampheylborane in ethyl alcohol at −35° C. The reactants were well mixed together and left at −35° C., without stirring, for 12 hours. The crystalline dialkylborane was isolated, washed with cold (−35° C.) ethyl alcohol (2×5 ml) and dried to yield 5.24 g (21.3 mmol, 85% yield) of 89% optically pure dialkylborane. The material was then suspended in 16 ml of tetrahydrofuran so as to give a 1.0M slurry and allowed to age for 12 hours at 0° C. The supernatant solution was decanted using a double-ended needle. The solid isopinocampheyl-(1S,2S)-trans-2-methylcyclohexylborane was washed with cold (0° C.) ethyl alcohol (2×3 ml) and dried to yield 4.66 g (18.9 mmol, 75% yield). The dialkylborane was methanolyzed, oxidized and worked up following the method of Brown, H. C. et al, *J. Org. Chem* 1981, 46, 2988. The resulting (1S,2S)-trans-methylcyclohexanol was purified using column d to furnish a gas chromotagraphy pure sample: $[\alpha]^{23}D$ +42.9° (0.1) c 1, MeOH), ≧99% optical purity.

EXAMPLE 5

Preparation of Isopinocampheyl-[S]-3-methyl-2-butylborane

Following the method of Example 1, 3.2 ml (30 mmol) of 2-methyl-2-butene was added to 34.6 ml (25 mmol) of 0.723M monoisopinocampheylborane in ethyl alcohol at −35° C. The reactants were mixed together and left at −35° C., without stirring, for 12 hours. The crystalline diborane was isolated, washed with cold (−35° C.) ethyl ether (2×3 ml) and dried to yield 3.97 g of product (18 mmol, 72% yield). The dialkylborane was 89% optically pure. It was cooled to −35° C. and 18.5 ml of tetrahydrofuran was added to it so as to give a 0.8M slurry. The reaction mixture was then allowed to age for 12 hours at −35° C. The supernatant solution was decanted using a double-ended needle. The solid isopinocampheyl-[S]-3-methyl-2-butylborane was washed with cold (−35° C.) ethyl ether and dried to yield 2.82 g (12.8 mmol, 51% yield) of product. The 3-methyl-2-butanol, obtained following alkaline hydrogen peroxide oxidation according to the method of Brown, H. C. et al. *J. Org. Chem.* 43, 5074 (1978), was purified using column d to give a gas chromotagraphy pure material: $[\alpha]^{23}D$ +4.97°±0.01 (neat), 100% optical purity.

EXAMPLE 6

Preparation of Dimethyl Alkylboronate Esters of High Optical Purity (1S,2S)-(+)-Dimethyl-trans-methyl-cyclopentylboronate was obtained by adding acetaldehyde (4 ml, 75 mmol) to a suspension of isopinocampheyl-(1S,2S)-trans-2-methylcyclopentylboronate prepared by the method of Example 2 (25 mmol) in 20 ml of ethyl ether at 0° C. After the vigorous initial reaction, 2 ml of acetaldehyde was added and the reaction mixture was stirred at 25° C. for 6 hours. Water (5 ml) was added and stirred for 0.5 hour. Excess acetaldehyde was evaporated (25° C., 12 mm Hg, 1 h) and pentane (30 ml) was added. The boronic acid was extracted with 3M sodium hydroxide (3×15 ml) in a separating funnel. The combined aqueous phase was cooled to 0° C., acidified with a 3M hydrochloride acid, extracted with ethyl ether (3×25 ml) and dried over anhydrous magnesium sulfate. Ethyl ether was evaporated and the boronic acid was reesterified with methanol following the procedure of Brown, H. C., et al., *Organometallics* 2, 1311 (1983.) The resulting ester was purified by distillation to yield 2.73 g (70% yield); bp 72°–74° C. (16 mm Hg); $[\alpha]^{24}D$ +51.56° (c 1, MeOH), 99% optical purity.

EXAMPLE 7

Preparation of trans-(2-Methylcyclopentyl)boronate and trans-2-Methylcyclopentanol of 100% ee A 50 mL centifuge vial vitted with a rubber septum and a magnetic stirring bar was charged with 34.6 mL of (−)-monoisopinocampheylborane (IpcBH, 100% ee) in ethyl ether (0.723M, 25 mmol) and cooled to −35° C. 1-Methylcyclopentene (3.2 mL, 30 mmol) was added to it. The reactants were mixed together well and the vial was left at −35° C. without stirring for 12 hours. The supernatant solution was decanted with the use of a double-ended needle. the crystalline isopinocampheyl-trans-(2-methylcyclopentyl)borane was washed with cold (−35° C.) ethyl ether (2×5 mL) and dried at 25° C. under reduced pressure (12 mm Hg), 3.79 g (16.3 mmol, 65% yield). The dialkylborane was methanolized, oxidized and worked up following literature procedures. The trans-2-methylcyclopentanol obtained was purified by using column d to furnish a GC-pure material: $[\alpha]^{25}D$ +46.8° (neat), 100% ee. The intermediate IpcR*BH was converted into dimethyl trans-(2-methylcyclopentyl)boronate, bp 85° C. at 0.05 mm, $[\alpha]^{25}D$+32.9° (c 7.8, THF), 100% ee.

EXAMPLE 8

Preparation of Dimethyl-trans-(2-Methylcyclohexyl)boronate and trans-2-Methylcyclohexanol in 100% ee With the experimental set up of Example 7, 3.5 mL (30 mmol) of 1-methylcyclohexene was added to 34.6 mL (25 mmol) of 0.723M monoisopinocampheylborane in ethyl ether at −35° C. The reactants were mixed together well and left at −35° C. without stirring for 12 hours. The crystalline dialkylborane was isolated, washed with cold (−35° C.) ethyl ether (2×5 mL) and dried to provide 5.24 g (21.3 mmol), 85% yield). the dialkylborane was 89% optically pure. It was suspended in 16 mL of tetrahydrofuran so as to give a 1.0M slurry and allowed to age for 12 hours at 0° C. The supernatant solution was decanted with use of a double-ended needle. The solid isopinocampheyl-trans-(2-methylcyclohexyl)borane was washed with cold (0° C.) ethyl ether (2×3 mL) and dried, 4.66 g (18.9 mmol, 75% yield). The dialkylborane was methanolized, oxidized and worked up following the literature procedure. The trans-2-methylcyclohexanol obtained was purified on column d to furnish a GC-pure sample: $[\alpha]^{23}D$ +42.9° (±0.1) (c 1, MeOH), 99% ee.

The intermediate IpcR*BH was converted into dimethyl trans-(2-methylcyclohexyl)boronate, bp 80°–81°

C. at 15 mm, $[\alpha]^{23}D$ +41.5° C. (c 15.4 in THF), ≧99% ee.

EXAMPLE 9

Preparation of dimethyl 2-butylboronate and 2-butanol of 100% ee

Diisopinocampheyl-sec-butylborane was prepared following the method of H. C. Brown et al, JACS 86, 397 (1964). Oxidation with alkaline hydrogen peroxide of an aliquot of this material gave 2-butanol of 95-98% ee. The tetrahydrofuran solvent was removed and the diisopinocampheyl-sec-butylborane dissolved in pentane. On cooling to −78° C., pure white crystals were obtained. The crystallization was repeated 5 times. An aliquot of the final product was oxidized. It revealed $[\alpha]^{25}D$ +5.35° (neat, 1=0.5) for 2-butanol. The product was treated with formaldehyde to form dimethyl 2-butylboronate, bp 38° C. at 30 mm, $[\alpha]^{23}D$ 9.1° (c, 12.0 in THF), 100% ee.

EXAMPLE 10

Preparation of 2-Cyclohexenol of 100% ee

Diisopinocampheylborane was prepared by the method of H. C. Brown et al., Israel J. Chem. 15, 12 (1977) from (+)-α-pinene. To the stirred suspension of diisopinocampheylborane (25 mmol) in tetrahydrofuran at −25° C. was added dropwise 2.4 mL (25 mmol) of 1,3-cyclohexadiene. Monohydroboration of the diene was complete after stirring the reaction mixture at −25° C. for 12 hours, as indicated by the disappearance of the solid diisopinocampheylborane and $^{11}B$ NMR (δ+80) examination of the solution. The reaction mixture was oxidized with trimethylamine-N-oxide, giving a 92:8 mixture of (−)-2-cyclohexen-1-ol (94% ee) and 3-cyclohexen-1-ol. A second reaction mixture at −78° C. was treated with 25 mm of lithium tert-butyl. Isobutylene was formed and the organoborane was converted into the corresponding borohydride as represented by the following reaction scheme.

The solution was taken to room temperature and the solvents removed under vacuum. Dry pentane was added to dissolve the salt. On cooling to low temperature, a crystalline product separated. The product was collected, redissolved in ethyl ether, and treated with hydrogen chloride to regenerate the organoborane.

The organoborane was oxidized with trimethylene-N-oxide to yield (−)-2-cyclohexen-1-ol of greater than 99% ee.

EXAMPLE 11

Preparation of 2-butyl-1,3,2-dioxaborinane and 2-butanol in 100% ee

To a stirred suspension of 9.26 g of diisopinocampheylborane (32.3 mmol) containing a slight excess of α-pinene (4.8 mmol) in tetrahydrofuran (30 mL) at −25° C. was added 35 mmol of cis-butene. The reaction mixture was stirred at −25° C. for 12 hours. (Oxidation of a duplicate reaction mixture gave 2-butanol of 95% ee.) Then 6.4 mL (64.6 mmol) of benzaldehyde was added and the mixture maintained at 0° C. An additional portion of benzaldehyde (6.4 mL, 64.6 mmol) was added and the reaction mixture brought to 25° C. and maintained there for 2 days. $^{11}B$ NMR revealed the borinate:boronate ratio was 30:70. Water (5.5 mL) was added and the tetrahydrofuran removed at reduced pressure. To the residue 20 mL of n-pentane was added and the solution extracted with 3N NaOH (3×11 mL). The alkaline extracts were acidified with 6N HCl and the aqueous solution extracted with ethyl ether (3×25 mL). The ether extracts were dried over magnesium sulfate and the ether removed at reduced pressure. There was obtained 2.3 g of 2-butylboronic acid. This was treated with 2 mL of 1,3-propanediol in 15 mL of n-pentane. Water separated. The pentane layer was dried over magnesium sulfate. The solvent removed and the boronic ester, 2.98 g (21 mmol) was distilled: bp 64°-65° C. at 15 mm, $[\alpha]^{23}D$ −4.7+0.03 (c 7, THF), 100% ee. Oxidation of the boronic ester produced 2-butanol, $[\alpha]^{23}D$ −10.7° (neat, 1 −1.0).

EXAMPLE 12

Preparation of 3-hexyl-1,3,2-dioxaborinane and 3-hexanol of 100% ee cis-3-Hexene (32 mmol) was hydroborated by 31 mmol of diisopinocamphylborane at −25° C. following the procedure of Example 3. (Oxidation of a duplicate reaction mixture gives 3-hexanol of 93% ee). To the reaction mixture at −25° C. 63 mmol of acetaldehyde was added, followed by an additional 62 mmol at −5° C. The reaction mixture was brought to 25° C. and stirred for 72 hours. Then an additional 126 mmol of acetaldehyde was added. (The aldehyde undergoes a slow polymerization and is lost to the reaction.) After 14 days, the ratio of borinate:boronate was 40:60 ($^{11}B$ NMR). Tetrahydrofuran and excess aldehyde was removed under reduced pressure and 30 mL of n-pentane added to dissolve the reaction product. The pentane solution was extracted with 3N NaOH (4×8 ml). The combined alkaline extracts were acidified with 6M hydrochloric acid. The white boronic acid was taken up from the aqueous suspension with ethyl ether (2×30 mL). Treatment with trimethylene glycol in pentane gave a 70% yield of the ester, 2-hexyl-1,3,2-dioxaborinane, bp 92°-94° (15 mm), $[\alpha]$ D +0.87±0.01 (c 15, THF). Oxidation with alkaline hydrogen peroxide gave 3-hexanol, $[\alpha]$ D −7.50° (neat), >99% ee.

EXAMPLE 13

Preparation of dimethyl (+)-exo-Norbornylboronate and (−)-exo-Norborneal

In the usual reaction vessel under nitrogen, 33 mmol of norbornene was hydroborated at −25° C. with 33 mmol of diisopinocampheylborane in tetrahydrofuran (26 mL) in the presence of a slight excess of α-pinene (4.9 mmol). The reaction product was treated with acetaldehyde; 66 mmol was added at −25° C. and an additional 66 mmol was added at 0° C. The reaction mixture was then stirred for 2 days at 25° C. After 2 days, the borinate:boronate ratio was 45:55 ($^{11}B$ NMR). The tetrahydrofuran and excess acetaldehyde was removed under reduced pressure. n-Pentane (35 mL) was added and the pentane solution was extracted with 3M NaOH (4×11 mL). The alkaline extract was acidified with 6M HCl. The boronic acid separated. It was extracted with ethyl ether (3×25 ml). The recovered acid was esterified by methanol to produce dimethyl exo-norbornylboronate, bp 82°–84° C. at 15 mm. Oxidation with alkaline hydrogen peroxide produced 1.7 g of (−)-exo-norbornanol, purified by preparative gas chromotography: $[\alpha]^{23}D$ −4.9°, 97% ee (determined by the $^{31}P$ NMR of the phosphate ester. Reaction of dimethyl-(+)-exo-norbornylboranate with N,N,N,N-tetrakis(2-hydroxyethyl)ethylenediamine produces the corresponding solid ester. After several recrystallizations, exo-norbornyl boronic acid was recovered in 100% ee.

EXAMPLE 14

Preparation of N,N,N,N-Tetrakis(2-hydroxyethyl)ethylenediamine Ester of Tetrahydro-2H-3-pyranylboronate and (+)-3-Hydroxytetrahydro-2H-pyran of 100% ee To diisopinocampheylborane of high optical purity (25 mmol) in tetrahydrofuran, 2.3 mL (25 mmol) of dihydropyran (kept over anhydrous potassium carbonate overnight and distilled) was added dropwise at 0° C. and kept under magnetic stirring for 12 hours. By that time, the solid diisopinocampheylborane had disappeared. $^{11}B$ NMR of the reaction mixture showed a signal corresponding to trialkylborane ($\delta 87$). To this, 5.6 mL (100 mmol, 60% excess) of acetaldehyde was added and stirred at 25° C. for 6 hours. $^{11}B$ NMR of the reaction mixture showed a peak corresponding to boronate ($\delta 29.7$). Excess acetaldehyde was removed under vacuum (30 mm Hg). The boronate thus obtained could not be distilled, as it decomposed upon heating. The reaction mixture was oxidized using 25 ml of 3N sodium hydroxide and 3.75 mL of 30% hydrogen peroxide at 25° C. for 5 hours. To the crude reaction mixture 25 g of anhydrous potassium carbonate was added and the organic layer was separated. The aqueous layer was extracted with 3×15 ml of ether. The combined organic layer was washed with saturated sodium chloride solution and the organic layer was dried over anhydrous magnesium sulfate. Ether was evaporated. The crude reaction mixture was filtered through silica gel (column chromotagraph). Pentane eluents removed the α-pinene and the ether eluents yielded 3-hydroxytetrahydropyran. The alcohol was distilled to obtain (99% chemically pure) 2.012 g of pure sample, bp 90° C./20 mm, n D 1.4570. Yield: 80%. It was further purified by preparative gas chromotograph (20% Carbowax 20M, 120° C.) to obtain 100% chemically pure sample: $[\alpha]^{23}D$ +10.55° (neat).

Its optical purity was determined by $^{19}F$ NMR technique by making its Mosher ester in the usual manner: 86% ee. The optical purity of the boronic acid was upgraded to 100% by recrystallization of the 2:1 chelated ester formed by esterification with N,N,N,N-tetrakis(2-hydroxyethyl)ethylenediamine as described in Example 15 below.

EXAMPLE 15

Preparation of 3-Hydroxy-2H-Tetrahydropyran of 100% ee

Ethyl tetrahydro-2H-3-pyranyl boronate (crude), was prepared as described above in Example 14. α-Pinene was displaced by treatment with acetaldehyde and removed under vacuum at 0.5 mm of mercury for 6 hours. The boronate thus obtained was free from α-pinene. To it (25 mmol) 25 mL of ether, followed by 2.95 g of N,N,N,N-ethylenediaminetetraethanol in 15 ml of isopropanol was added and stirred at 25° C. for 1 hour. A white solid was crystallized out. It was filtered to obtain 5.5 g of boronate. Yield: 52% (starting from olefin). $^{11}B$ NMR: $\delta 37.2$, mp 81° C. The solid was taken in 13 mL of ether and to it 13 ml of 2N hydrochloric acid was added and stirred at 24° C. for 0.5 hour. The ether layer was removed by a double-ended needle and the aqueous layer was saturated with sodium chloride and extracted with 3×10 mL of ether. The combined organic layer was dried over anhydrous magnesium sulfate and the ether pumped off. A while crystalline solid, tetrahydro-2H-pyranylboronic acid was obtained. It was taken in 20 ml of ether and oxidized with 3N sodium hydroxide and 30% hydrogen peroxide. 3-Hydroxy-2H-tetrahydropyran thus obtained was distilled and further purified by preparative gas chromotagraphy to obtain 100% chemically pure sample: $[\alpha]^{23}D$ +11.93° C. (neat), 100% ee by $^{19}F$ NMR.

The above procedures were all carried out under nitrogen. For consistency, all reactions used (+)-α-pinene. The use of (−)-α-pinene gives products of the opposite rotation and the enantiomeric isomer.

The invention claimed is:

1. A process for upgrading to essentially 100% enantiomeric excess the optical purity of an organoborane intermediate represented by the formulae:

IpcBHR* or

Ipc$_2$BR* wherein Ipc is isopinocampheyl, and R* is alkyl having from 4 to 30 carbon atoms comprising the steps of:
 (a) reacting an alkene selected from the group consisting of a cis-alkene, trans-alkene or tertiary-alkene with a hydroborating agent selected from the group consisting of monoisopinocampheylborane and diisopinocampheylborane;
 (b) obtaining a solid intermediate; and
 (c) recrystallizing the resulting solid hydroboration product from a suitable solvent to obtain a monoisopinocampheylalkylborane or diisopinocampheylalkylborane of essentially 100% enantiomeric excess.

2. The process of claim 1 wherein said hydroboration product is recrystallized from a hydrocarbon or an ether solvent.

3. The process of claim 1 wherein said hydrocarbon solvent is pentane.

4. The process of claim 2 wherein said solvent is diethyl ether.

5. A process for upgrading to essentially 100% enantiomeric excess the optical purity of an organoborane intermediate represented by the formula:

IpcBHR*

Wherein Ipc is isopinocampheyl, and R* is alkyl having from 4 to 30 carbon atoms, comprising the steps of:
 (a) reacting a trans-alkene or a tertiary-alkene with monoisopinocampheylborane; and
 (b) obtaining a solid intermediate; and
 (c) recrystallizing the resulting hydroboration product from a suitable solvent to obtain a monoisopinocampheylalkylborane of essentially 100% enantiomeric excess.

6. The process of claim 5 wherein said hydroboration product is recrystallized in a hydrocarbon or an ether solvent.

7. The process of claim 6 wherein said hydrocarbon solvent is pentane.

8. The process of claim 6 wherein said ether solvent is diethyl ether.

9. A recrystallized monoisopinocampheylalkylborane of essentially 100% enantiomeric excess prepared by the process of claim 1, represented by the formula IpcBHR* wherein Ipc is isopinocampheyl and R* is alkyl having from 4 to 30 carbon atoms.

10. A process for upgrading to essentially 100% enantiomeric excess the optical purity of an organoborane intermediate prepared by hydroborating a cis-alkene with diisopinocampheylborane and represented by the formula Ipc$_2$BR* wherein Ipc is isopinocampheyl, and R* is alkyl having from 4 to 30 carbon atoms represented by the formula where the α-carbon is a new chiral center and where R$_1$ and R$_2$ are the same or different members of the group consisting of alkyl, cycloalkyl and aryl, said process comprising the steps of:
  (a) reacting a cis-alkene with diisopinocampheylborane;
  (b) obtaining a solid organoborane; and
  (c) recrystallizing said solid organoborane from a suitable solvent.

11. The process of claim 10 wherein said solvent is a hydrocarbon or an ether solvent.

12. The process of claim 11 wherein said hydrocarbon solvent is pentane.

13. The process of claim 11 wherein said ether solvent is diethyl ether.

14. A process for upgrading to essentially 100% enantiomeric excess the optical purity of an organoborane intermediate prepared by hydroborating a cis-alkene with diisopinocampheylborane and represented by the formula Ipc$_2$BR* wherein Ipc is isopinocampheyl, and R* is an alkyl group having from 4 to 30 carbon atoms represented by the formula where the α-carbon is a new chiral center and where R$_1$ and R$_2$ are the same or different members of the group consisting of alkyl, cycloalkyl and aryl, said process comprising the steps of:

(a) reacting a cis-alkene with diisopinocampheylborane to obtain a non-solid borane hydroboration product;
  (b) converting said non-solid borane to a solid compound selected from the group consisting of a borate, a borane complex and a chelate by treatment with a compound selected from the group consisting of a strong base, an amine having low steric requirements and an aminoethanol chelating agent; and
  (c) recrystallizing said solid from a suitable solvent to obtain a diisopinocampheylalkylborane of essentially 100% enatiomeric excess.

15. The process of claim 14 wherein said non-solid borane is converted to a solid borate.

16. The process of claim 14 wherein said non-solid borane is converted to a solid borate by treatment with a strong base.

17. The process of claim 16 wherein said strong base is an alkali metal base.

18. The process of claim 14 wherein said non-solid borane is converted to a solid borane complex.

19. The process of claim 14 wherein said non-solid borane is converted to a solid borane complex by treatment with an amine having low steric requirements.

20. The process of claim 18 wherein said non-solid borane is converted to a borinic acid by treatment with an equivalent of aldehyde and the borinic ester is converted to a solid chelate.

21. The process of claim 20 wherein said non-solid borane is converted to a solid chelate by treatment of said borinic ester with an aminoethanol chelating agent.

22. The process of claim 21 wherein said aminoethyl chelating agent is selected from the group consisting of ethanolamine, N-methylethanolamine, 2-pyrrolidinemethanol and 2-pyridyl-2-methanol.

23. A bore intermediate of essentially 100% enantiomeric excess prepared by recrystallization by the process of claim 1 and represented by the formula:

Ipc$_2$BH wherein Ipc is isopinocampheyl and R* is where the α-carbon is a new chiral center and where R$_1$ and R$_2$ are the same or different members of the group consisting of a alkyl, cycloalkyl and aryl.

24. A process for upgrading to essentially 100% enantiomeric excess the optical purity of organoborane intermediates prepared by hydroborating a trans-alkene or tertiary-alkene with monoisopinocampheylborane and represented by the formula:

IpcBHR* wherein Ipc is isopinocampheyl and R* is alkyl, cycloalkyl or aryl, said process comprising the steps of:
  (a) reacting a trans-alkene or tertiary-alkene with monoisopinocampheylborane to obtain a non-solid borane hydroboration product;
  (b) converting said non-solid borane so obtained to a solid selected from the group consisting of a borate, a boron complex and a chelate by treatment with a compound selected from the group consisting of a strong base, an amine having low steric requirements and an aminoethyl chelating agent; and (c) recrystallizing said solid from a suitable solvent to obtain a monoisopinocampheylalkylborane of essentially 100% enantiomeric excess.

25. The process of claim 24 wherein said non-solid borane is converted to a solid borate.

26. The process of claim 24 wherein said non-solid borane is converted to a solid borate by treatment with a strong base.

27. The process of claim 26 wherein sad strong base is an alkali metal base.

28. The process of claim 24 wherein said non-solid borane is converted to a solid borane complex.

29. The process of claim 24 wherein said non-solid borane is converted to a solid borane complex by treatment with an amine having low steric requirements.

30. The process of claim 28 wherein said non-solid borane is converted to a borinic acid by treatment with an equivalent of aldehyde and the borinic ester is converted to a solid chelate.

31. The process of claim 30 wherein said non-solid borane is converted to a solid chelate by treatment of said borinic ester with an aminoethanol chelating agent.

32. The process of claim 31 wherein said aminoethyl chelating agent is selected from the group consisting of ethanolamine, N-methylethanolamine, 2-pyrrolidinemethanol and 2-pyridyl-2-methanol.

* * * * *

UNITED STATES PATENT AND TRADEMARK OFFICE
CERTIFICATE OF CORRECTION

PATENT NO. : 4,713,380

DATED : December 15, 1987

INVENTOR(S) : Herbert C. Brown

It is certified that error appears in the above-identified patent and that said Letters Patent is hereby corrected as shown below:

In Claim 23, line 1, "bore" should read --borane--.

Signed and Sealed this

Fourteenth Day of February, 1989

Attest:

DONALD J. QUIGG

Attesting Officer   Commissioner of Patents and Trademarks